United States Patent [19]

Braun

[11] Patent Number: 5,409,502
[45] Date of Patent: Apr. 25, 1995

[54] HAIR DYE COMPOSITION CONTAINING A 4'-AMINO-2-HALOGEN-4-{BIS-(-HYDROX-YETHYL)AMINO} AZOBENZENE COMPOUND

[75] Inventor: Hans J. Braun, Ueberstorf, Switzerland

[73] Assignee: Wella Aktiengesellschaft, Darmstadt, Germany

[21] Appl. No.: 157,206

[22] PCT Filed: Mar. 25, 1993

[86] PCT No.: PCT/EP93/00722
§ 371 Date: Dec. 9, 1993
§ 102(e) Date: Dec. 9, 1993

[87] PCT Pub. No.: WO93/25182
PCT Pub. Date: Dec. 23, 1993

[30] Foreign Application Priority Data

Jun. 17, 1992 [DE] Germany .................. 42 19 738.4

[51] Int. Cl.$^6$ ................................ A61K 7/13
[52] U.S. Cl. ............................ 8/405; 8/429; 8/662; 8/666
[58] Field of Search ............... 8/405, 429, 662, 666, 8/639; 534/630, 676, 857

[56] References Cited

U.S. PATENT DOCUMENTS

| | | | |
|---|---|---|---|
| 1,850,155 | 5/1930 | Reddelien et al. | 534/857 |
| 2,172,752 | 7/1937 | Kvalnes | 534/857 |
| 3,985,499 | 12/1976 | Lang et al. | 8/10.1 |
| 4,297,098 | 10/1981 | Dasher et al. | 8/412 |

FOREIGN PATENT DOCUMENTS 2282860 3/1976 France .
2165257 4/1986 United Kingdom .

OTHER PUBLICATIONS

Indian J. Fibre Text. Res., vol. 15, Jun. 1990, pp. 76–80, "Synthesis and dyeing characteristics of mono- and bis-. . ."

J. C. Johnson, "Hair Dyes", 1973, pp. 3–91 and 113–139.

Primary Examiner—Paul Lieberman
Assistant Examiner—Caroline L. Dusheck
Attorney, Agent, or Firm—Michael J. Striker

[57] ABSTRACT

The compositions for dyeing hair contains at least one 4'- amino-2-halogen-4-[bis-($\beta$-hydroxyethyl)amino]azobenzene. The hair dye compositions according to the invention have a good resistance to acids and provide a wide assortment of natural and fashion shades.

10 Claims, No Drawings

HAIR DYE COMPOSITION CONTAINING A 4′-AMINO-2-HALOGEN-4-{BIS-(-HYDROXYETHYL)AMINO} AZOBENZENE COMPOUND

BACKGROUND OF THE INVENTION

The subject matter of the invention is a composition for dyeing hair containing a 4′-amino-2-halogen-4-[bis-(β-hydroxyethyl)amino]azobenzene.

Along with oxidative hair dyes formed by oxidative coupling of one or more developers, direct-dyeing hair dyes are becoming increasingly important for dyeing hair. Direct hair dyes offer the advantage that they can be applied without the addition of oxidizing agents (for example hydrogen peroxide) and therefore cause considerably less damage to the hair during the dyeing process.

Good hair dye compositions must satisfy a number of requirements. For example, they must create the desired shade with sufficient intensity and at the same time be absorbed in the hair without excessive discoloration of the scalp. Further, the hair dyeing must possess sufficient fastness to light, heat, perspiration, hair cleaning agents, and the chemicals used for permanent waving. They must also be stable when acted on by acidic agents and diluted acids. Finally, these compositions should be unobjectionable in toxicological and dermatological respects.

Since a uniform coloring of the hair from the root to the tip of the hair is generally impossible with dyes of a single class of compounds, combinations of dyes from a number of different classes of compounds are normally used—for example, dye combinations containing azo and anthraquinone dyes in addition to derivatives of amino-, diamino-, and hydroxyamino-nitrobenzenes.

The most commonly used azo dye is 4′-amino-4-[bis-(β-hydroxyethyl)amino]azobenzene (DISPERSE BLACK 9). It is also known from DE-OS 35 34 885 to use 4′-amino-2-methyl-4[bis-(β-hydroxyethyl)amino]azobenzene as a hair dye.

Although often used in hair dye compositions, the 4′-amino-4-[bis-(β-hydroxyethyl)amino]azobenzene is not completely satisfactory in technical respects relating to application. On the one hand, this compound is suspected of mutagenic behavior. On the other hand, hair dyeing produced by this compound and by the hair dyes known from DE-OS 35 34 885 have a poor stability relative to acids and acidic preparations.

SUMMARY OF THE INVENTION

Therefore, it is an object of the present invention to provide hair dye compositions containing an azo dye which have good physiological compatibility and produce coloring which is stable under acids and acidic preparations, e.g. acidic hair rinses or hair cleaning agents, acidic permanent wave compositions and fixatives, and which therefore enable a long-lasting dyeing of hair which remains constant over longer periods of time.

It has now been found that this problem is solved in an outstanding manner by a composition for dyeing hair containing a 4′-amino-2-halogen-4-[bis(β-hydroxyethylamino]-azobenzene.

The subject matter of the present invention is therefore a composition for dyeing hair containing conventional additives for hair dye compositions which is characterized in that it contains at least one 4′-amino-2-halogen-4-[bis-(β-hydroxyethylamino]azobenzene of the general formula (I)

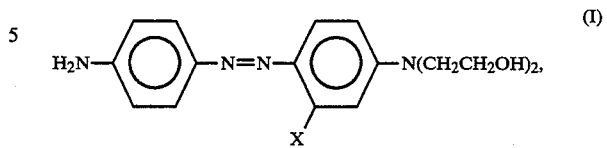

where X equals fluorine, chlorine or bromine.

Of the compositions according to the invention, the composition containing 4′-amino-2-chloro-4-[bis-(β-hydroxyethyl)amino]azobenzene is preferred. The dyes of general formula (I) are contained in the composition according to the invention in concentrations of 0.01 to 2 percent by weight, preferably in concentrations of 0.01 to 1 percent by weight.

The hair dye according to the invention is a composition containing at least one dye of the general formula (I) or a composition containing one or more additional dyes which are absorbed directly in the hair, in addition to at least one dye of the general formula (I). Of these dyes which are absorbed directly in the hair, the following are mentioned by way of example: aromatic nitro dyes such as 2-amino-6-chloro-4-nitrophenol, 2-amino-4,6-dinitrophenol, 4-[(β-hydroxyethyl)amino]-2-nitroaniline, 2-chloro-6-ethylamino-4-nitrobenzene, $N^1$, $N^4$, $N^4$-tris(β-hydroxyethyl)-p-phenylenediamine (HC BLUE 2), 4-[Bis-(β-hydroxyethyl)-amino]-1-methylamino-2-nitrobenzene, 1-[(2,3-dihydroxypropyl)amino]-4-ethyl-[(2-hydroxyethyl)amino]-2-nitrobenzene, 1-[(2,3-dihydroxypropyl)amino]-4-dimethylamino-2-nitrobenzene, 1-[(2,3-dihydroxypropyl)amino]-2-nitro-4-pyrrolidinobenzene, 4-[Bis-(β-hydroxyethyl)amino]-1-[(3-hydroxypropyl)amino]-2-nitrobenzene, 2-amino-4-nitrophenol, 2-nitro-1,4-diaminobenzene, 2-amino-5-nitrophenol, 2-amino-5-[(β-hydroxyethyl)amino]nitrobenzene, 4-(β-hydroxyethyl)amino-3-nitrophenol, 1-(β-hydroxyethyl)amino-2-amino-4-nitrobenzene, 4-(β-ureidoethyl)aminonitrobenzene, 4-(2′3′-dihydroxypropyl)amino-3-nitrotrifluoromethylbenzene, 1,4-bis[(β-hydroxyethyl)amino]-4-N-ethyl-2-nitrobenzene, 4-(β-hydroxyethyl)amino-3-nitrotoluene, 2,5-bis-[(β-hydroxyethyl)amino]nitrobenzene, 2-(β-hydroxyethyl)amino-4,6-dinitrophenol, 1-amino-4-(2′3′-dihydroxypropyl)amino-2-nitro-5-chlorobenzene, 1-amino-2-nitro-4-[bis-(β-hydroxyethyl)amino]benzene; triphenylmethane dyes, e.g. Basic Violet 1 (C.I. 42,535), Basic Violet 14 (C.I. 42,510), Basic Violet 2 (C.I. 42,520); azo dyes such as Acid Brown 4 (C.I. 14,805); anthraquinone dyes, e.g. 1-[(β-hydroxyethyl)amino]- 4-methylamino anthraquinone (DISPERSE BLUE 3, C.I. 61,505), DISPERSE BLUE 23 (C.I. 61,545), 1,4-diaminoanthraquinone (DISPERSE VIOLET 1, C.I. 61,100), and 1,4,5,8-tetraaminoanthraquinone (C.I. 64,500). The dyes of these classes, depending on their constituents, can have an acidic, nonionic or basic character. Other suitable dyestuffs which are absorbed directly in the hair are described, for example, in J C Johnson, "Hair Dyes", Noyes Data Corp., Park Ridge, USA (1973), pages 3–91 and 113–139 (ISBN: 0-8155-0477-2).

The total amount of hair dye contained in the composition is preferably 0.01 to 3.0 percent by weight.

The preparation form of the hair dye composition described herein, which is also often called a tinting composition, can be a solution, particularly an aqueous or aqueous-alcoholic solution. Other preferred preparation forms are cream, gel, emulsion or foam. It can also be mixed with a propellant or sprayed by a pump.

The pH of this dyeing composition ranges from 3 to 12, particularly p8 to 11.5. The desired alkaline pH value is most often adjusted with ammonia, but this can also be done with organic amines such as monoethanolamine or triethanolamine.

The hair dye composition described here is usually used by applying an amount of this composition to the hair sufficient for dyeing the hair. The composition remains in contact with the hair for approximately 5 to 30 minutes. The hair is subsequently rinsed with water and, if necessary, also with an aqueous solution of weak organic acid, and is then rinsed and dried. Examples of such weak organic acids are acetic acid, citric acid, tartaric acid and the like.

The hair dye composition according to the invention can take the form of a hair dye composition with additional hair setting agents containing at least one polymerizate or natural polymer conventionally used in cosmetics. Such compositions are commonly known as tinting setting agents or color setting agents.

Of the polymerizates known for this purpose in cosmetics, the following are mentioned by way of example: polyvinylpyrrolidone, polyvinyl acetate, polyvinyl alcohol or polyacrylic compounds such as polyacrylic acid and polymethacrylic acid, basic polymerizates of the ester of polyacrylic acid or polymethacrylic acid with amino alcohols or their salts or quaternization products, polyacrylonitrile, polyvinyl lactams and copolymerizates of these compounds such as polyvinylpyrrolidone vinyl acetate and the like.

Natural polymers such as chitosan (deacetylated chitin) or chitosan derivatives can also be used for this purpose.

The polymerizates and natural polymers are contained in the hair dye composition described above in quantities usually used for such compositions, i.e. approximately 1 to 5 percent by weight. The pH of the composition ranges from approximately 6.0 to 9.0. The use of this hair dye composition with additional setting agent is effected in a known and conventional manner by moistening the hair with the setting agent, setting the hair for styling, and subsequent drying.

If desired, the hair dye composition described above can, of course, also contain other conventional ingredients for hair dye compositions such as preservatives and perfume oils, solvents such as water, lower aliphatic alcohols, e.g. ethanol, propanol and isopropanol or glycols such as glycerin and 1,2-propylene glycol, and also wetting agents or emulsifiers from the classes of anionic, cationic, amphoteric or nonionic surface-active substances such as fatty alcohol sulfates, alkylsulfonates, alkylbenzenesulphates, alkyltrimethylammonium salts, alkyl betaines, ethoxylated fatty alcohols, ethoxylated nonylphenols, fatty acid alkanolamides, ethoxylated fatty acid esters, as well as thickeners such as higher fatty alcohols, starch or cellulose derivatives, petrolatum, paraffin oil and fatty acids, grooming materials such as cationic resins, lanolin derivatives, cholesterol, pantothenic acid and betaine. The aforementioned ingredients are used in the usual quantities for such purposes, e.g. the wetting agents and emulsifiers in concentrations of approximately 0.5 to 30 percent by weight, the thickeners in quantities of approximately 0.1 to 25 percent by weight and the grooming materials in concentrations of approximately 0.1 to 5.0 percent by weight.

The compounds of formula (I) contained in the hair dye compositions described herein are unobjectionable in toxicological and dermatological respects and achieve hair coloring with excellent resistance to acids and acidic preparations.

Depending on their type and the composition of the dye components, these hair dyes offer a wide range of different shades ranging from natural shades to highly-fashionable, luminescent hues.

The subject matter of this application also includes the new compounds 4'-amino-2-fluoro-4-[bis-($\beta$-hydroxyethyl)amino]azobenzene and 4'-amino-2-bromo-4-[bis-($\beta$-hydroxyethyl)amino]azobenzene.

As is the case with 4'-amino-2-chloro-4-[bis-($\beta$-hydroxyethyl)amino]azobenzene, these new compounds can be produced in two steps according to the following reaction equation (X=F, Cl, Br):

Step 1:

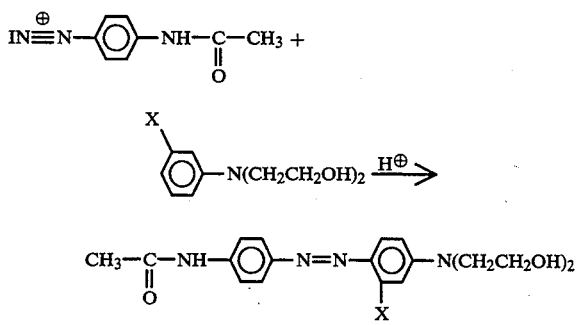

Step 2:

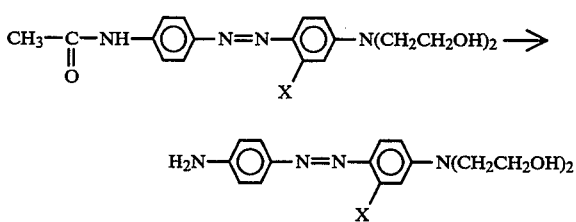

The production process is carried out as follows:

When the fluorine compound is used, an equimolar amount of 3-halogen-N,N-bis-($\beta$-hydroxyethyl)aniline is added slowly over ice by drops to an aqueous solution of the diazonium salt of p-phenylenediamine-N-monoacetate in an acidic medium. When the chlorine or bromine compounds are used, the aqueous solution of the diazonium salt is added by drops to an equimolar amount of the 3-halogen-N,N-bis-($\beta$-hydroxyethyl)aniline over ice. The reaction mixture is then stirred for 24 hours at room temperature.

The reaction product is then either filtered out or the reaction mixture is extracted with diethyl ether and the ether extract is evaporated in a vacuum. The resulting 4'-(acetylamino)-2-halogen-4-[bis-($\beta$-hydroxyethyl)amino]azobenzene is then heated in a mixture of ethanol and concentrated hydrochloric acid (ratio of ethanol to HCl=5: 2) or ethanol and 2n-sodium hydroxide (ratio of ethanol to sodium hydroxide =1:1) for several hours under reflux. The reaction mixture is then cooled to 0° Celsius, diluted with water, and neutralized with a 25-percent ammonia solution. The resulting 4'-amino-2-halogen-4-[bis-($\beta$-hydroxyethyl)amino]azobenzene is then extracted with diethyl ether, the ether extract is reduced in a vacuum, and the resulting product is purified if necessary.

The following examples will explain the subject matter of the present invention in more detail without limiting the invention to these examples:

PRODUCTION EXAMPLES

Example 1

Production of 4'-amino-2-fluoro-4-[bis-(β-hydroxyethyl)amino]azobenzene

Step 1

Production of 4'-(acetylamino)-2-fluoro-4-[bis-(β-hydroxyethyl)amino]azobenzene

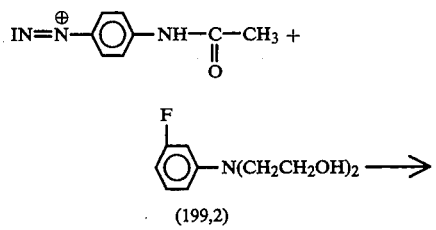

(199,2)

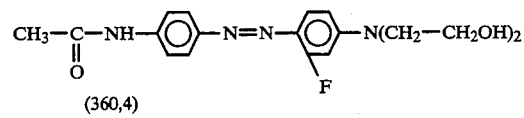

(360,4)

3 g (0.02 moles) p-phenylenediamine-N-monoacetate are diazotized in a mixture of 10 g water, 30 g crushed ice, and 3.4 ml concentrated hydrochloric acid with 1.5 g (0.022 moles) sodium nitrite at 0° C. A solution of 3.98 (0.02 moles) 3-fluoro-N,N-bis-(β-hydroxyethyl)aniline in 16 ml water and 3.4 ml concentrated hydrochloric acid is then added by drops to the solution of diazonium salt within two hours accompanied by stirring and cooling over ice.

The reaction mixture is then stirred for 16 hours at room temperature and neutralized with ammonia (pH=7.5). The reaction product is in the form of a dark brown precipitate. It is filtered out, washed with water and dried over calcium chloride.

The yield is 4.87 g (=67.6% of the theoretical yield).

| CHN analysis: (C₁₈H₂₁F N₄O₃) | % C | % H | % N |
|---|---|---|---|
| estimated: | 59.99 | 5.87 | 15.55 |
| actual: | 58.62 | 5.74 | 15.10 |

Step 2

Production of 4'-amino-2-fluoro-4-[bis-(β-hydroxyethyl)amino]azobenzene

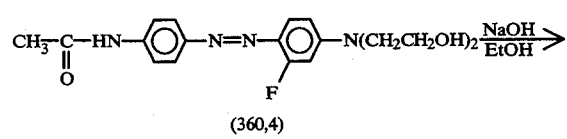

(360,4)

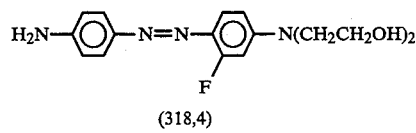

(318,4)

0.5 g (1.4 mmoles) 4'-(acetylamino)-2-fluoro-4-[bis-(β-hydroxyethyl)amino]azobenzene are heated in a mixture of 7.5 ml ethanol and 7.5 ml 2n-sodium hydroxide for four hours under reflux. The reaction mixture is then poured over 50 g crushed ice, the orange precipitate is filtered off, washed with water, and dried over calcium chloride.

The yield is 0.35 g (=78.5% of the theoretical yield).
The melting point is 147° to 149° C.

| CHN analysis: (C₁₆H₁₉FN₄O₂ × H₂O) | % C | % H | % N |
|---|---|---|---|
| estimated: | 57.13 | 6.29 | 16.66 |
| actual: | 57.71 | 5.93 | 16.45 |

Example 2

Production of 4'-amino-2-bromo-4-[bis-(β-hydroxyethyl)amino]azobenzene

Step 1

Production of 4'-(acetylamino)-2-bromo-4-[bis-(β-hydroxyethyl)amino]azobenzene

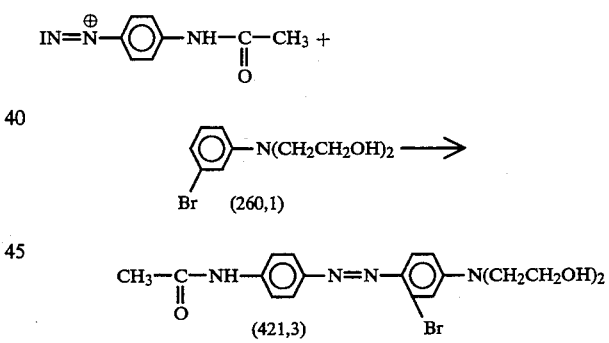

15 g (0.1 mole) p-phenylenediamine-N-monoacetate are diazotized in a mixture of 50 g water, 150 g crushed ice, and 17 ml concentrated hydrochloric acid with 7.6 g (0.11 moles) sodium nitrite at 0° C. The solution of diazonium salt is filtered and the filtrate is added by drops to a cooled solution of 26 g (0.1 mole) 3-bromo-N,N-bis-(β-hydroxyethyl)aniline in 80 ml water and 17 ml concentrated hydrochloric acid within two hours accompanied by stirring.

The reaction mixture is then stirred for 24 hours at room temperature. The precipitate is then filtered out and dried in a desiccator over calcium chloride.

9.5 g (=20% of the theoretical yield) 4'-(acetylamino-2-bromo-4-[bis-(β-hydroxyethyl)amino]azobenzene hydrochloride hemihydrate are obtained.

The melting point of this product is 187° to 189° C. (accompanied by decomposition).

CHN analysis:
(C₁₈H₂₁BrN₄O₃ × HCl × ½ H₂O)

| | % C | % H | % N | % Br | % Cl |
|---|---|---|---|---|---|
| estimated: | 46.28 | 4.53 | 12.00 | 16.94 | 7.61 |
| actual: | 46.60 | 4.80 | 10.80 | 17.10 | 7.90 |

Step 2

Production of 4'-amino-2-bromo-4-[bis-(β-hydroxyethyl)amino]azobenzene

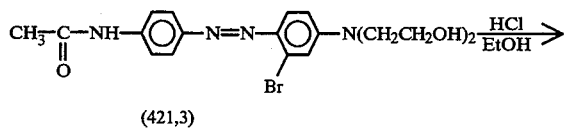

(421,3)

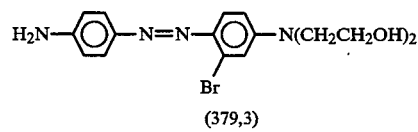

(379,3)

8.4 g (0.02 moles) 4'-(acetylamino)-2-bromo-4-[bis-(β-hydroxyethyl)amino]azobenzene are heated in a mixture of 100 ml ethanol and 40 ml concentrated hydrochloric acid for four hours under reflux. The reaction mixture is then cooled to 0° C., mixed with 200 ml water and neutralized with a 25-percent ammonia solution.

The solution is then extracted with diethyl ether and the ether extract is dried over magnesium sulfate and filtered. After evaporating the ether extract, 6.4 g (=84% of the theoretical yield) of a red oil are obtained which slowly crystallizes. The melting point of the crystalline product is 120° to 124° C.

CHN analysis:
(C₁₆H₁₉BrN₄O₂)

| | % C | % H | % N |
|---|---|---|---|
| estimated: | 50.67 | 5.05 | 14.77 |
| actual: | 50.79 | 5.14 | 14.57 |

Example 3

Production of 4'-amino-2-chloro-4-[bis-(β-hydroxyethyl)amino]azobenzene

Step 1

Production of 4'-(acetylamino)-2-chloro-4-[bis-(β-hydroxyethyl)amino]azobenzene

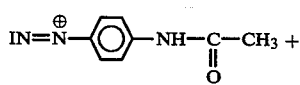

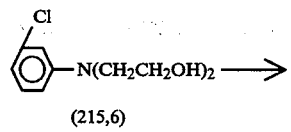

(215,6)

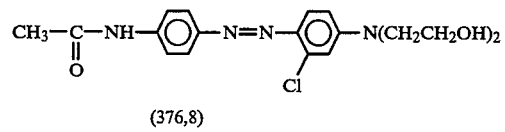

(376,8)

15 g (0.1 mole) p-phenylenediamine-N-monoacetate are diazotized in a mixture of 50 g water, 150 g crushed ice, and 17 ml concentrated hydrochloric acid with 7.6 g (0.11 moles) sodium nitrite at 0° C. The solution of diazonium salt is filtered and the filtrate is added by drops to a cooled solution of 21.6 g (0.1 mole) 3-chloro-N,N-bis-(β-hydroxyethyl)aniline in 80 ml water and 17 ml concentrated hydrochloric acid within two hours accompanied by stirring.

The reaction mixture is then stirred for 24 hours at room temperature. The precipitate is then filtered out and dried in a desiccator over calcium chloride.

8.3 g (=20% of the theoretical yield) 4'-(acetylamino-2-chloro-4-[bis-(β-hydroxyethyl)amino]azobenzene hydrochloride are obtained.

The melting point of this product is 192° C. (accompanied by decomposition).

Step 2

Production of 4'-amino-2-chloro-4-[bis-(β-hydroxyethyl)amino]azobenzene

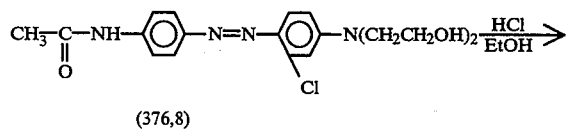

(376,8)

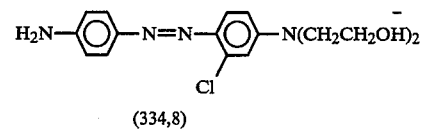

(334,8)

7.5 g (0.02 moles) 4'-(acetylamino)-2-chloro-4-[bis-(β-hydroxyethyl)amino]azobenzene are heated in a mixture of 100 ml ethanol and 40 ml concentrated hydrochloric acid for four hours under reflux.

The reaction mixture is then cooled to 0° C., mixed with 200 ml water and neutralized with a 25-percent ammonia solution.

The solution is then extracted with diethyl ether and the ether extract is dried over magnesium sulfate and filtered. After evaporating the ether extract, 5.2 g (=77.6% of the theoretical yield) of a slowly crystallizing red oil are obtained.

The melting point after recrystallization in toluene is 146° to 148° C.

CHN analysis:
(C₁₆H₁₉ClN₄O₂)

| | % C | % H | % N |
|---|---|---|---|
| estimated: | 57.40 | 5.72 | 16.73 |
| actual: | 57.55 | 5.78 | 16.68 |

Examples for hair dye compositions

Example 4

Hair dye solution

| | |
|---|---|
| 0.3 g | 4'-amino-2-halogen-4-[bis-(β-hydroxyethyl)-amino]azobenzene of the general formula (I) |
| 2.0 g | lauryl alcohol diglycol ether sulfate sodium salt (28-percent aqueous solution) |
| 2.0 g | ammonia (25-percent aqueous solution) |
| 10.0 g | isopropanol |
| 85.7 g | water |
| 100.0 g | |

Bleached human hair is treated for 20 minutes at room temperature with this hair dye solution. The hair is then rinsed with water and dried. The hair is dyed as indicated in the following table.

TABLE 1

Hair dyes

| Type of 4'-amino-2-halogen-4-[bis-(β-hydroxyethyl)amino]azobenzene used | hair color |
|---|---|
| 4'-amino-2-fluoro-4-[bis-(β-hydroxyethyl)-amino]azobenzene | orange |
| 4'-amino-2-chloro-4-[bis-(β-hydroxyethyl)-amino]azobenzene | orange |
| 4'-amino-2-bromo-4-[bis-(β-hydroxyethyl)-amino]azobenzene | intense orange |

Example 5

Hair dye cream

| | |
|---|---|
| 0.04 g | 4'-amino-2-chloro-4-[bis-(β-hydroxyethyl)-amino]azobenzene |
| 0.30 g | $N^1,N^4,N^4$-tris-(β-hydroxyethyl)-2-nitro-p-phenylenediamine |
| 0.03 g | 1-nitro-4-[2-ureidoethyl)amino]benzene |
| 0.02 g | Disperse Blue 3 (C.I. 61,505) |
| 0.02 g | Disperse Violet 1 (C.I. 61,100) |
| 0.02 g | 4-[(2-hydroxyethyl)amino]-2-nitroaniline |
| 7.00 g | cetyl alcohol |
| 2.00 g | lauryl alcohol diglycol ether sulfate sodium salt (28-percent aqueous solution) |
| 0.20 g | ammonia (25-percent aqueous solution) |
| 0.10 g | p-hydroxybenzoic acid methyl ester |
| 90.27 g | water |
| 100.0 g | |

50 g of the preceding hair dye composition are applied to white human hair, allowed to act for 20 minutes, and rinsed out with water.

The hair is then dried. The hair treated in this way is dyed a natural brown shade.

Example 6

Hair dye solution

| | |
|---|---|
| 0.05 g | 4'-amino-2-chloro-4-[bis-(β-hydroxyethyl)-amino]azobenzene |
| 0.05 g | 1,4-diaminoanthraquinone |
| 0.10 g | $N^1,N^4,N^4$-tris-(β-hydroxyethyl)-2-nitro-p-phenylenediamine |
| 10.00 g | ammonia (25-percent aqueous solution) |
| 5.00 g | lauryl alcohol diglycol ether sulfate sodium salt (28-percent aqueous solution) |
| 0.50 g | hydroxyethyl cellulose |
| 10.00 g | isopropanol |
| 74.30 g | water |
| 100.0 g | |

Bleached natural human hair is treated for 20 minutes at room temperature with the preceding hair dye solution. The hair is then rinsed with water and washed with a shampoo. After drying, the hair has an ash-blond color.

Example 7

Comparison tests for resistance to acids

To compare the resistance to acid of the 4'-amino-2-halogen-4-[bis-(β-hydroxyethyl)amino]azobenzene with the 4'-amino-4-[bis-(β-hydroxyethyl)amino]azobenzenes known from the prior art, strands of natural hair were dyed as described in Example 4 using the following hair dye compositions:

(i) a composition according to Example 4 (X=Cl), (ii) a composition according to Example 4 in which the 4'-amino-2-chloro-4-[bis-(β-hydroxyethyl)amino]-azobenzene was replaced by an equal amount of 4'-amino-4-[bis-(β-hydroxyethyl)amino]azobenzene, (iii) a composition according to Example 4 in which the 4'-amino-2-chloro-4-[bis-(β-hydroxyethyl)amino]-azobenzene was replaced by an equal amount of 4'-amino-2-methyl-4-[bis-(β-hydroxyethyl)amino]-azobenzene, (iv) a composition according to Example 4 (X=F).

The strands of hair which were dyed in this way were either (A) treated with 1n-hydrochloric acid for 1 minute and then washed with an acidic shampoo (pH =5.5) and dried or (B) treated for 4 hours with a solution of 10 g sodium chloride and 1 g sodium dihydrogen phosphate in 1000 ml water adjusted to a pH of 3 with 2n-hydrochloric acid, then rinsed with water and dried.

The laboratory color values of the hair strands dyed in this way were determined by a Minolta color measurement device, Type CR-200. The determined laboratory color values are compiled in the following table:

TABLE 2

Color measurement washing tests with acids

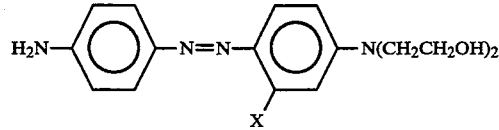

| | | (A) | | (B) | |
|---|---|---|---|---|---|
| X | | not treated | 1n-hydrochloric acid | not treated | buffer pH = 3 |
| (i) Cl | L | 65.1 | 56.8 | 64.9 | 66.2 |
| | a | 40.2 | 23.7 | 39.1 | 36.7 |
| | b | 82.7 | 70.4 | 81.8 | 83.2 |
| (ii) H | L | 58.8 | 37.5 | 66.8 | 64.4 |
| | a | 41.7 | 6.0 | 33.1 | 25.1 |
| | b | 77.3 | 38.1 | 85.0 | 79.7 |
| (iii) $CH_3$ | L | 70.1 | 45.3 | 65.5 | 57.7 |
| | a | 26.8 | −1.4 | 35.8 | 21.2 |
| | b | 87.1 | 41.0 | 82.5 | 67.1 |
| (iv) F | L | 69.2 | 68.8 | 70.1 | 69.7 |
| | a | 24.8 | 19.7 | 24.2 | 19.8 |
| | b | 82.4 | 76.3 | 84.2 | 80.3 |

Table 2 shows that the measured color values of the strands of hair treated with the composition (i, iv) according to the invention are reduced substantially less when treated with acids than the strands treated with the known compounds (ii, iii).

The substantially improved resistance to acid of the hair dye composition according to the invention compared to the prior art becomes even more apparent if the total change in color $\Delta Y$ is calculated according to Anderson (cf. US-PS 5,000,755) based on the following equation:

$$\Delta Y = \sqrt{(\Delta L)^2 + (\Delta a)^2 + (\Delta b)^2}$$

The values determined for the total change in color $\Delta Y$ are compiled in Table 3:

TABLE 3

Total change in color $\Delta Y$

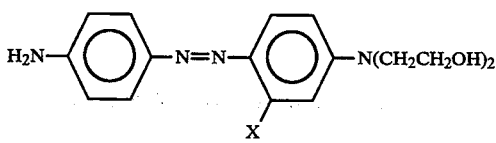

(I)

| X | (A) 1n-hydrochloric acid | (B) buffer pH = 3 |
|---|---|---|
| (i) Cl | 22.2 | 3.1 |
| (ii) H | 57.1 | 9.9 |
| (iii) CH$_3$ | 59.5 | 22.6 |
| (iv) F | 8.0 | 5.9 |

The strands of hair treated with the composition according to the invention (i, iv) show a substantially smaller total change in color ($\Delta Y$) when acted upon by 1n-hydrochloric acid than the hair strands treated with the known compositions (ii, iii).

When treated with an acidic (pH=3) buffer solution, the measured color values of the strands of hair treated with the compositions (i, iv) according to the invention do not change, whereas the strands treated with the known hair dye compositions (ii, iii) show a distinct change in color.

All percentages represent percent by weight unless otherwise indicated.

I claim:

1. Composition for dyeing hair containing at least one conventional ingredient for hair dye compositions selected from the group consisting of solvents, preservatives, perfume oils, synthetic emulsifiers, thickeners, and grooming materials, and from about 0.01 to 3.0 percent by weight of at least one [4'-amino-2-halogen-4-(bis-($\beta$-hydroxyethylamino]azobenzene]4'-amino-2-halogen-4-{bis-($\beta$-hydroxyethyl)amino}azobenzene of the formula (I)

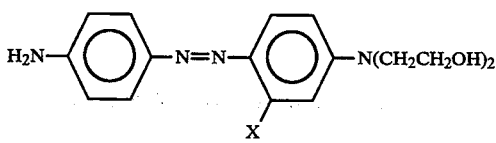

(I)

where X is selected from the group consisting of fluorine, chlorine and bromine.

2. Composition according to claim 1, containing 4'-amino-2-chloro-4-[bis-($\beta$-hydroxyethyl)amino]azobenzene.

3. Composition according to claim 1, containing 0.01 to 2 percent by weight of said 4'-amino-2-halogen-4-{bis-($\beta$-hydroxyethyl)amino}azobenzene of formula (I).

4. Composition according to claim 1, having a pH of 3 to 12.

5. Composition according to claim 1, in the form of an aqueous or aqueous-alcoholic solution, a cream, gel, emulsion or foam.

6. Composition according to claim 1, containing at least one additional direct hair dye.

7. Composition according to claim 6, wherein said at least one direct hair dye is selected from the group consisting of 2-amino-6-chloro-4-nitrophenol, 2-amino-4,6-dinitrophenol, 4-[($\beta$-hydroxyethyl)amino]-2-nitroaniline, 2-chloro-6-ethylamino-4-nitrobenzene, N$^1$,N$^4$,N$^4$-tris-($\beta$-hydroxyethyl)-p-phenylenediamine (HC BLUE 2), 4-[bis-($\beta$-hydroxyethyl)amino]-1-methylamino-2-nitrobenzene, 1-[(2,3-dihydroxypropyl)amino)-4-ethyl-[(2-hydroxyethyl)amino]-2-nitrobenzene, 1-[(2,3-dihydroxypropyl)amino]-4-dimethylamino-2-nitrobenzene, 1-((2,3-dihydroxypropyl)-amino]-2-nitro-4-pyrrolidinobenzene, 4-[bis-($\beta$-hydroxyethyl)amino)-1-[(3-hydroxypropyl)amino]-2-nitrobenzene, 2-amino-4-nitrophenol, 2-nitro-1,4-diaminobenzene, 2-amino-5-nitrophenol, 2-amino-5-[($\beta$-hydroxyethyl)amino]nitrobenzene, 4-($\beta$-hydroxyethyl)amino-3-nitrophenol, 1-($\beta$-hydroxyethyl)amino-2-amino-4-nitrobenzene, 4-($\beta$-ureidoethyl)aminonitrobenzene, 4-(2',3'-dihydroxypropyl)-amino-3-nitrotrifluoromethylbenzene, 1,4-bis-[($\beta$-hydroxyethyl)amino]-4-N-ethyl-2-nitrobenzene, 4 -($\beta$-hydroxyethyl)amino-3 -nitrotoluene, 2,5-bis-[($\beta$-hydroxyethyl)amino]nitrobenzene, 2-($\beta$-hydroxyethyl)amino-4,6-dinitrophenol, 1-amino-4-(2',3'-dihydroxypropyl)amino-2-nitro-5-chlorobenzene, 1-amino-2-nitro-4-[bis-($\beta$-hydroxyethyl)amino]benzene, Basic Violet 1 (C.I. 42,535), Basic Violet 14 (C.I. 42,510), Basic Violet 2 (C.I. 42,520), Acid Brown 4 (C.I. 14,805), 1-[($\beta$-hydroxyethyl)amino]-4-methylaminoanthraquinone, Disperse Blue 23 (C. I. 61,545), 1,4-diaminoanthraquinone and 1,4,5,8-tetraaminoanthraquinone.

8. Composition according to claim 1, further comprising additional hair setting agents and at least one member selected from the group consisting of polymerizates and natural polymers conventionally used in cosmetics.

9. Composition according to claim 8, wherein said member is selected from the group consisting of polyvinylpyrrolidone, polyvinyl acetate, polyvinyl alcohol, polyacrylic acid, polymethacrylic acid, basic polymerizates of esters of polyacrylic acid and polymethacrylic acid with amino alcohols, salts of said basic polymerizates and quaternization products of said basic polymerizates, polyacrylonitrile, polyvinyl lactams and copolymerizates thereof and chitosan and chitosan derivatives.

10. Composition according to claim 1, wherein said at least one conventional ingredient is selected from the group consisting of fatty alcohol sulfates, alkylsulfonates, alkylbenzenesulphates, alkyltrimethylammonium salts, alkyl betaines, ethoxylated fatty alcohols, ethoxylated nonylphenols, fatty acid alkanolamides, ethoxylated fatty acid esters, fatty alcohols, starch and cellulose derivatives, petrolatum, paraffin oil and fatty acids, cationic resins, lanolin derivatives, cholesterol, pantothenic acid and betaine.

* * * * *